United States Patent
Bergner et al.

(10) Patent No.: US 6,481,847 B1
(45) Date of Patent: Nov. 19, 2002

(54) TESTING AND CALIBRATING DEVICE FOR OPTICAL EYE LENGTH MEASUREMENT INSTRUMENTS

(75) Inventors: Roland Bergner, Jena (DE); Lothar Mueller, Ottendorf (DE)

(73) Assignee: Carl Zeiss Jena GmbH, Jena (DE)

( * ) Notice: Subject to any disclaimer, the term of this patent is extended or adjusted under 35 U.S.C. 154(b) by 46 days.

(21) Appl. No.: 09/631,517

(22) Filed: Aug. 3, 2000

(30) Foreign Application Priority Data

Aug. 3, 1999 (DE) .......................... 199 36 571

(51) Int. Cl.$^7$ ................................. A61B 3/00
(52) U.S. Cl. ....................................... 351/200
(58) Field of Search ............................. 351/200, 205, 351/212, 216, 221; 359/15, 16; 600/310, 476; 422/50, 52

(56) References Cited

U.S. PATENT DOCUMENTS 5,535,743 A * 7/1996 Backhaus et al. ........... 600/310
6,042,785 A * 3/2000 Harju .......................... 422/52

FOREIGN PATENT DOCUMENTS

DE          43 13 031 A1   10/1994
DE         195 04 465 A1    8/1996

OTHER PUBLICATIONS

*English Abstract of DE 195 04 465 A1.
*English Abstract of DE 43 13 031 A1.
* cited by examiner Primary Examiner—George Manuel
(74) Attorney, Agent, or Firm—Reed Smith LLP

(57) ABSTRACT

A testing and calibrating device for optical eye length measurement devices comprising two plano-convex lenses which are arranged in the illumination beam path so as to be oppositely oriented. A neutral filter with a defined transmission is located between these two plano-convex lenses.

12 Claims, 1 Drawing Sheet

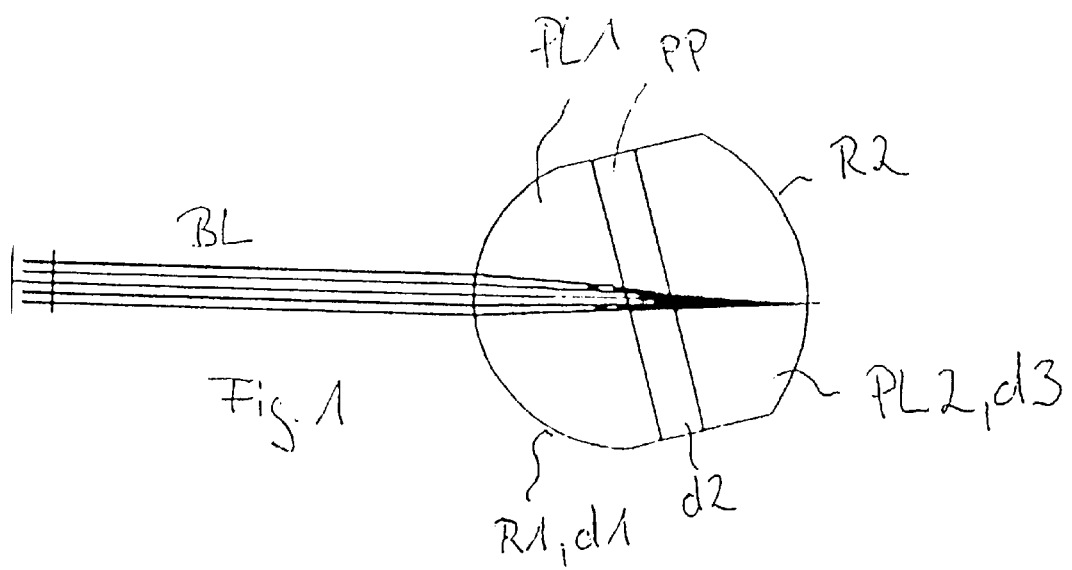

TESTING AND CALIBRATING DEVICE FOR OPTICAL EYE LENGTH MEASUREMENT INSTRUMENTS

BACKGROUND OF THE INVENTION a) Field of the Invention

The present invention relates to a testing and calibrating device for optical eye length measurement devices.

b) Description of the Related Art

A spherical transparent test body which is preferably made of glass, has coatings and a refractive index of approximately 2 is known as a testing and calibrating device for optical eye length measurement instruments (EP-A 509903, U.S. Pat. No. 5,347,327, U.S. Pat. No. 5,347,328) from DE 19504465 A1 by the present Applicant. The coating, chiefly of the back of the test body, involves a costly technique and difficult technology.

OBJECT AND SUMMARY OF THE INVENTION

Therefore, the primary object of the present invention is a test body for optical eye length measurement devices that is simple to produce but is universally applicable.

In accordance with the invention, a testing and calibrating device for optical eye length measurement devices comprises two plano-convex lenses which are arranged in the illumination beam path so as to be oppositely oriented. A neutral filter with a defined transmission is located between these two plano-convex lenses.

BRIEF DESCRIPTION OF THE DRAWINGS

In the drawings:

FIG. I shows a schematic view of the test body.

DESCRIPTION OF THE PREFERRED EMBODIMENTS

Relative to FIG. 1:

The test body comprises three individual parts in the direction of illumination of the eye in an eye length measurement device according to the prior art cited above:

- a first plano-convex lens PL1 which can be approximately or exactly hemispherical
- a plane plate PP made of gray filter or neutral density filter material
- a second plano-convex lens PL2.

The parallel illumination light BL is bundled through the first lens PL1 and focussed on the back of the second lens PL2. The accuracy of this test ball intended for axial length measurement is determined by the thickness values matching the refractive indices and by the two radii.

The cementing of the individual parts is carried out by edge alignment, for which reason the edge cylinders are fabricated in a highly precise register.

In order to prevent reflections, principally at the plane plate, the entire arrangement is utilized at an angle (advantageously between 10 and 20 degrees). The input surface radius is set at around 7 mm analogous to the corneal surface of the human eye.

The thickness of the first lens is determined in an advantageous manner with respect to manufacturing technique for hemispherical expansion. The thickness of the neutral density filter plate is calculated for the actual oblique beam path through the plane plate (15-degree beam inclination in our example), wherein the forward path and return path are to be added, namely, in such a way that the desired value for the total reflectivity is achieved for the entire system after reflecting at the rear radius and exiting at the first radius (around 7 mm), the transmission at the neutral density filter plate in the forward and return path multiplied by the reflection at the rear radius approximately determines the total reflectivity at $$\text{Transmission } T = 0.23^{d_{forward}+d_{return}} \times ((n-1)/(n+1))^2,$$

where 0.23 is the net transmittance, the value for the utilized NG3 neutral density filter glass for 1 mm glass path length, n is the index of refraction of the rear lens PL2, and dforward and dreturn are the thicknesses traversed for the forward and return path (they are approximately equal).

The approximate transmission was determined for the useful wavelength (780 nm) at $8.2 \times 10^{-5}$.

The thickness of the rear lens must be determined in such a way that the intersection for the main beam of the utilized bundle diameter is located on the rear radius.

The rear radius is determined by adding the respective wavelengths of the main beam through the front lens, neutral density filter and rear lens in relation to air.

The entire arrangement can be centered after cementing such that it is suitably received in a mechanical mount so that it is used at an angle such that reflections are eliminated at the neutral density filter plate.

An arrangement dimensioned in this way reflects the incident beam bundle in itself, even with small angular changes in the position of the test ball, without disturbing secondary reflections, as would be had in a comparable test ball with the refractive index 2 for this wavelength with a reflectivity of the above-indicated value for the rear ball surface which could only be produced, if at all, with an expensive special coating.

By using another neutral density filter or varying its thickness at the expense of the rear lens thickness, another test ball can be dimensioned effortlessly. Accordingly, test balls which simulate different turbidity values due to eye cataract can be advantageously produced.

Preferably, a ball is used which simulates an eye without turbidity and without defective vision (T=approximately $10^{-4}$) and a ball with $T=10^{-9}$ which corresponds to an eye with high turbidity due to cataract.

These two balls are used specifically for testing the functionality of the axial length measuring instrument (particularly the internal electronic amplification). In must be possible to process large and small measurement signals in a corresponding manner. Further, the balls can be utilized for training in the operation of the device and for regular monitoring of the constancy of measurements. The front surface of the balls is designed in such a way that the corneal radius measurement function can also be tested (training and quality assurance).

By varying the tilt of the beam path, an accurate degree of absorption can also be advantageously adjusted because a tilt by an amount of approximately five degrees means a transmission correction of about 20–25%, since the beam length is changed in the neutral density filter.

---

Test ball for normal eye: ($\tau = 10^{-4}$)

| front hemisphere | plane plate PP | rear hemisphere |
| --- | --- | --- |
| PL1 | | PL2 |

-continued radius of curvature:

R1 = 7.182  
Glass type: SLF6  NG3  R2 = 9.172  
thickness: d1 = 7.182  d2 = 2.1  SFL6  
Test ball, weak for high cataract: ($\tau = 10^{-9}$)  d3 = 6.54

PL1  PP  PL2  
radius of curvature:

R1 = 7.182  
Glass type: SLF6  NG10  R2 = 9.172  
thickness: d1 = 7.182  d2 = 2.3  SFL6  
  d3 = 6.3

While the foregoing description and drawings represent the preferred embodiments of the present invention, it will be obvious to one skilled in the art that various changes and modifications may be made therein without departing from the true spirit and scope of the present invention.

What is claimed is:

1. A testing and calibrating device for optical eye length measurement devices comprising:
    two plano-convex lenses which are arranged in an illumination beam path so as to be oppositely oriented; and
    a neutral filter with a defined transmission being located between these two plano-convex lenses.

2. The testing and calibrating device according to claim 1, wherein the neutral filter is a parallel plate.

3. The testing and calibrating device according to claim 1, wherein the piano-convex lenses are essentially hemispherical.

4. The testing and calibrating device according to claim 1, wherein the piano-convex lenses and plane plate are cemented together.

5. The testing and calibrating device according to claim 1, wherein the plano-convex lenses and neutral filter are made of glass.

6. The testing and calibrating device according to claim 2, wherein the parallel plate is arranged in the device at an angle to the illumination axis.

7. The testing and calibrating device according to claim 1, wherein the radius of the first lens is approximately 7 mm.

8. The testing and calibrating device according to claim 1, wherein a plurality of test bodies with different transmission are used to simulate different eye turbidity in the device.

9. An arrangement according to claim 1, wherein the transmission is adjusted by changing the tilt angle of the testing device in the measurement beam path.

10. A method for using the testing aid calibrating device of claim 1, including the step of adjusting the transmission by changing; the tilt angle of the testing and calibrating device the measurement beam path.

11. A test ball for simulating a normal eye comprising the following elements:

| front hemisphere radius of curvature: | ($\tau = 10^{-4}$) plane plate PP | rear hemisphere |
|---|---|---|
| R1 = 7.182 glass type: SLF6 thickness: d1 = 7.182 | NG3 d2 = 2.1 | R2 = 9.172 SFL6 d3 = 6.54 |

12. A test ball for simulating a high-r cataract comprising the following elements: (T=$10^{-9}$)

| front hemisphere radius of curvature: | plane plate | rear hemisphere |
|---|---|---|
| R1 = 7.182 glass type: SLF6 thickness: d1 = 7.182 | NG10 d2 = 2.3 | R2 = 9.172 SFL6 d3 = 6.3 |

* * * * *